US009402559B2

United States Patent
Imai et al.

(10) Patent No.: US 9,402,559 B2
(45) Date of Patent: Aug. 2, 2016

(54) INPUT DEVICE AND CALIBRATION METHOD

(71) Applicant: Sony Corporation, Tokyo (JP)

(72) Inventors: Hirokazu Imai, Chiba (JP); Yoichi Toriumi, Tokyo (JP); Hideo Kawabe, Saitama (JP); Kenichi Kabasawa, Saitama (JP); Tatsuya Suzuki, Kanagawa (JP); Masatoshi Ueno, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 244 days.

(21) Appl. No.: 13/689,083

(22) Filed: Nov. 29, 2012

(65) Prior Publication Data

US 2013/0150697 A1     Jun. 13, 2013

(30) Foreign Application Priority Data

Dec. 9, 2011 (JP) .................................. 2011-269831

(51) Int. Cl.
| | |
|---|---|
| A61B 5/04 | (2006.01) |
| A61B 5/0492 | (2006.01) |
| A61B 5/0488 | (2006.01) |
| A61B 5/11 | (2006.01) |
| A61B 5/22 | (2006.01) |
| A61B 5/00 | (2006.01) |

(52) U.S. Cl.
CPC .............. *A61B 5/0492* (2013.01); *A61B 5/0488* (2013.01); *A61B 5/11* (2013.01); *A61B 5/04012* (2013.01); *A61B 5/1124* (2013.01); *A61B 5/1125* (2013.01); *A61B 5/224* (2013.01); *A61B 5/4082* (2013.01); *A61B 5/6824* (2013.01); *A61B 5/72* (2013.01); *A61B 5/721* (2013.01); *A61B 5/7221* (2013.01); *A61B 5/7267* (2013.01); *A61B 5/7275* (2013.01); *A61B 5/7282* (2013.01)

(58) Field of Classification Search
CPC ............. A61B 5/0488; A61B 5/04012; A61B 5/1124; A61B 5/1125; A61B 5/72; A61B 5/721; A61B 5/6824; A61B 5/224; A61B 5/7267; A61B 5/7221; A61B 5/7275; A61B 5/7282; A61B 5/4082; A61B 5/0492
USPC ........................................................ 600/546
See application file for complete search history.

(56) References Cited

U.S. PATENT DOCUMENTS

2009/0326406 A1 * 12/2009 Tan .......................... G06F 1/163
                                                                    600/546

FOREIGN PATENT DOCUMENTS

JP         2002-287869       10/2002

* cited by examiner

*Primary Examiner* — Devin Henson
(74) *Attorney, Agent, or Firm* — Chip Law Group

(57) ABSTRACT

There is provided an input device including a plurality of electrodes that are arranged on a surface of a body in a direction crossing a muscular fiber group of the body at a right angle, and detect electromyogram signals generated from the muscular fiber group according to a motion performed by the body; a switch unit that switches an electrode acquiring an electromyogram signal between the plurality of electrodes; and a control unit that selects an electrode detecting an electromyogram signal for identifying the motion from among the plurality of electrodes.

9 Claims, 8 Drawing Sheets

INPUT DEVICE AND CALIBRATION METHOD

CROSS REFERENCES TO RELATED APPLICATIONS

The present application claims priority to Japanese Priority Patent Application JP 2011-269831 filed in the Japan Patent Office on Dec. 9, 2011, the entire content of which is hereby incorporated by reference.

BACKGROUND

The present disclosure relates to an input device and a calibration method.

Recently, research has been being conducted on a device that identifies a motion of a body using an electromyogram signal generated in accordance with motion of muscles and performs input to an apparatus. It is necessary for devices that have been proposed thus far to accurately determine the positions of electrodes installed at some desired muscles. In particular, when the electrodes are installed on an arm or a leg, a thickness or a muscle attachment method varies according to person, and thus there is a problem of difficulty in determining accurate positions. In addition, there is a problem that relative positions of skin to which an electrode is attached and a muscle deviate from each other due to motions in and outside a cycle, and thus the degree of precision in motion identification deteriorates.

In response to such problems, Japanese Unexamined Patent Application Publication No. 2002-287869 proposes a method of identifying a motion of a body based on distribution of electromyogram signals obtained from a plurality of electrodes.

SUMMARY

However, in the technology of Japanese Unexamined Patent Application Publication No. 2002-287869, it is necessary to handle signals of all the electrodes for motion identification, and the load of a device is increased when a large amount of signals are processed.

For this reason, the present disclosure proposes an input device and a calibration method that are capable of reducing load involved in signal processing.

According to an embodiment of the present disclosure, there is provided an input device including a plurality of electrodes that are arranged on a surface of a body in a direction crossing a muscular fiber group of the body at a right angle, and detect electromyogram signals generated from the muscular fiber group according to a motion performed by the body, a switch unit that switches an electrode acquiring an electromyogram signal between the plurality of electrodes, and a control unit that selects an electrode detecting an electromyogram signal for identifying the motion from among the plurality of electrodes.

Further, according to another embodiment of the present disclosure, there is provided a calibration method including time-divisionally detecting electromyogram signals while switching between a plurality of electrodes that are arranged on a surface of a body in a direction crossing a muscular fiber group of the body at a right angle and detect the electromyogram signals generated from the muscular fiber group according to a motion performed by the body, and selecting at least one electrode detecting an electromyogram signal for identifying the motion based on the respective electromyogram signals acquired by the plurality of electrodes.

According to still another embodiment of the present disclosure, a plurality of electrodes that are arranged on a surface of a body in a direction crossing a muscular fiber group of the body at a right angle, detect electromyogram signals generated from the muscular fiber group according to a motion performed by the body, a switch unit switches an electrode acquiring an electromyogram signal between the plurality of electrodes, and a control unit selects an electrode detecting an electromyogram signal for identifying the motion from among the plurality of electrodes.

According to the embodiments of the present disclosure described above, it is possible to reduce load involved in signal processing.

Additional features and advantages are described herein, and will be apparent from the following Detailed Description and the figures.

DETAILED DESCRIPTION

Figure 1A:
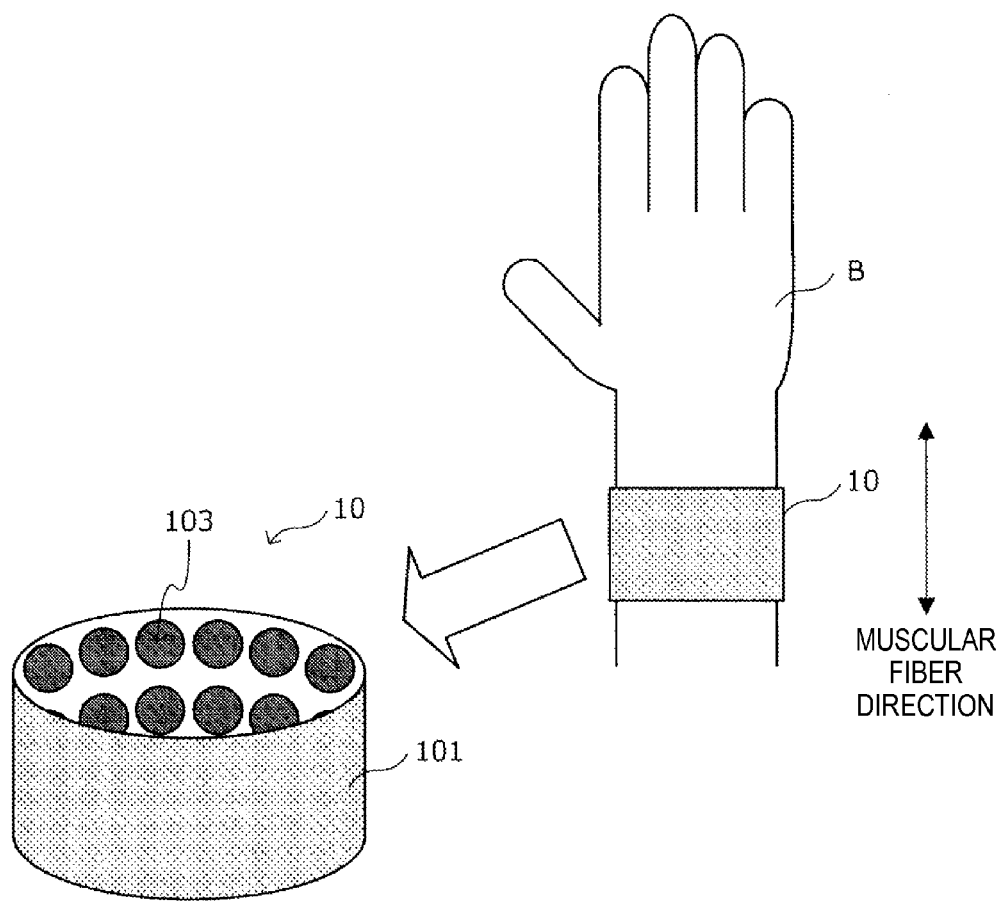
FIG. 1A is an explanatory diagram typically illustrating an input device related to a first embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Descriptions will be given in the following order.
(1) First Embodiment
(1-1) Regarding Input Device
(1-2) Regarding Calibration Method and Input Method
(1-3) Detailed Examples of Calibration Method and Simple Calibration Method
(1-4) Modified Example
(2) Summary

First Embodiment

Figure 1B:
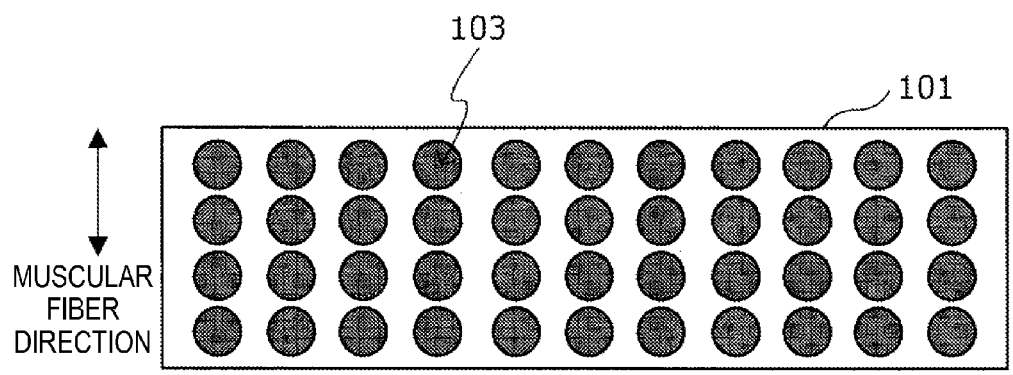
FIG. 1B is an explanatory diagram typically illustrating the input device related to the same embodiment.
Figure 2:
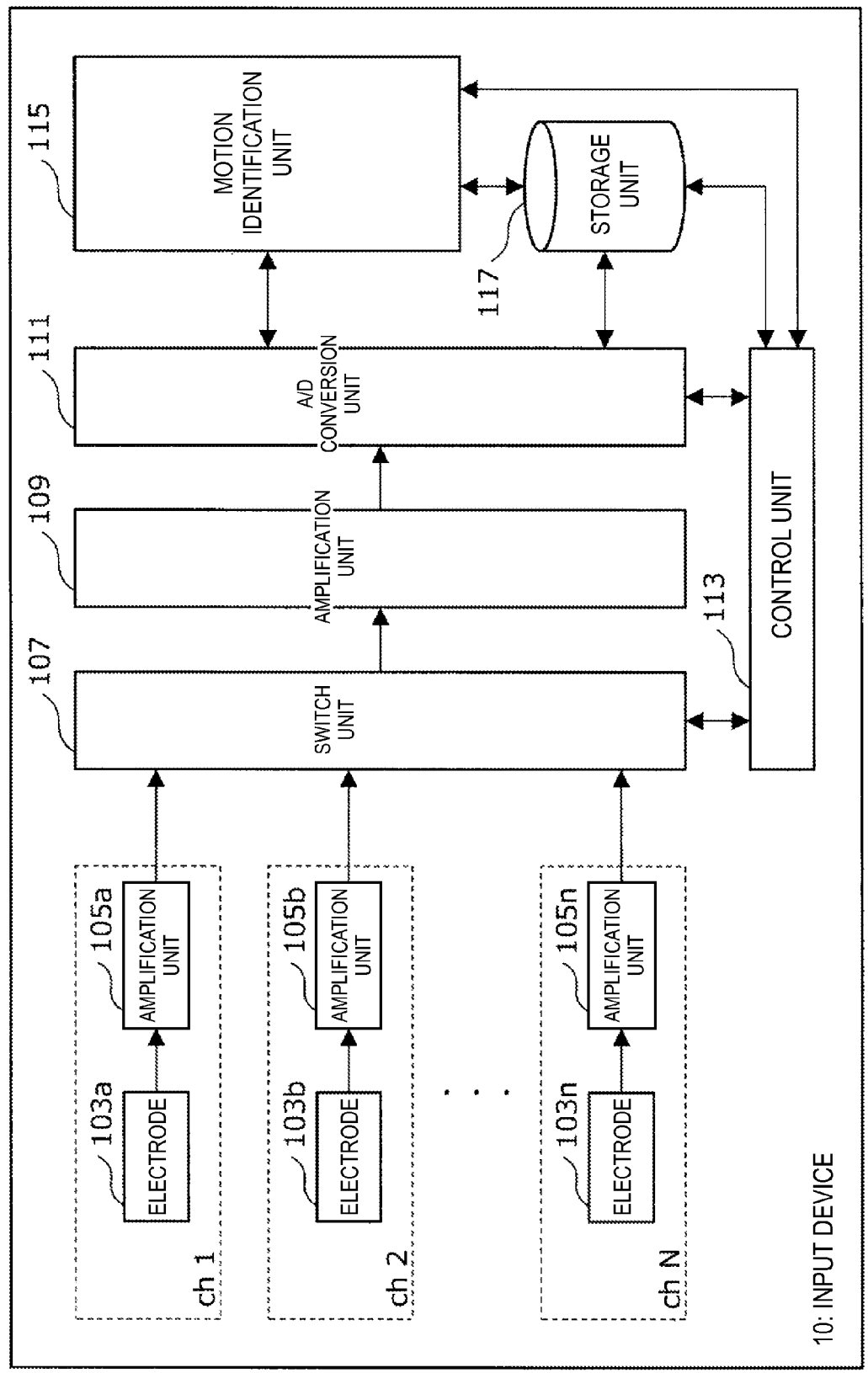
FIG. 2 is a block diagram showing an example of a configuration of the input device related to the same embodiment.

[Regarding Input Device]
First, an input device related to a first embodiment of the present disclosure will be described in detail with reference to FIG. 1A to FIG. 2. FIG. 1A and FIG. 1B are explanatory diagrams typically illustrating an input device related to this embodiment, and FIG. 2 is a block diagram showing an example of a configuration of the input device related to this embodiment.

[Regarding Appearance of Input Device]

In an input device 10 related to this embodiment, as shown in FIG. 1A, a plurality of electrodes 103 are disposed on a substrate 101 having flexibility, and the input device 10 is disposed on a body surface B (a forearm part in FIG. 1A) so that an electrode-arranged surface of the substrate 101 faces the body surface B. As the substrate 101, an arbitrary material that has flexibility so that the electrodes 103 and the like can be arranged thereon can be used. Also, the electrodes 103 can be appropriately selected from among all well-known electrodes according to a size of the substrate 101 in which the electrodes 103 are installed, necessary detection sensitivity, or the like.

On or in the substrate 101, electronic devices, such as a Central Processing Unit (CPU), a Read Only Memory (ROM), a Random Access Memory (RAM), an Integrated Circuit (IC), a microprocessor, a transistor, a condenser, a resistor, a diode, and the like, a wired/wireless communication device, a variety of interconnections, or the like not shown in the drawings are present, and these devices interoperate with each other, thereby implementing functions of the input device 10 which will be described later.

FIG. 1B typically illustrates the input device 10 of FIG. 1A that is unfolded in a circumferential direction of the forearm. As shown in FIG. 1B, in the input device 10 related to this embodiment, the plurality of electrodes 103 are arranged in a muscular fiber direction and the circumferential direction (in other words, a direction that crosses the muscular fiber direction at a right angle) of the forearm. Since the plurality of electrodes are arranged in the direction that crosses the muscular fiber direction at a right angle, it becomes possible to certainly detect electromyogram signals involved in a motion performed by the forearm. Also, since the plurality of electrodes are arranged in the muscular fiber direction, it is possible to more accurately detect electromyogram signals generated from a muscular fiber group that is present along the plurality of electrodes.

In the example shown in FIG. 1B, 11 electrodes are disposed in the circumferential direction of the forearm, but the number of electrodes arranged in the circumferential direction of the forearm can be set to an arbitrary number that is two or more. Also, in the example shown in FIG. 1B, four electrodes are disposed in the muscular fiber direction, but the number of electrodes arranged in the muscular fiber direction can be set to an arbitrary number that is two or more. In the example shown in FIG. 1B, the plurality of electrodes 103 are disposed at nearly the same intervals, but may not be disposed at the same intervals. In addition, in the example shown in FIG. 1B, the plurality of electrodes 103 are vertically and horizontally disposed in a lattice shape, but may be disposed in a diagonal pattern.

Here, each of the plurality of electrodes that are arranged in the circumferential direction of the forearm and the muscular fiber direction as shown in FIG. 1B may be used as one channel, or a group of a plurality of electrodes arranged in the muscular fiber direction (for example, two electrodes adjacent in the muscular fiber direction, or the like) may be used as one channel. When the group of a plurality of electrodes is handled as one channel, an electrode combination method (a method of setting the number of channels) can be appropriately determined. For example, as shown in FIG. 1B, when four electrodes are arranged in the muscular fiber direction and two electrodes are handled as one channel, the four electrodes may be combined into two channels two by two in an up-to-down order, or combined into three channels using the two intervening electrodes in common.

In the example shown in FIG. 1A, a case in which the input device 10 has a cylindrical shape is shown. However, the input device 10 related to this embodiment may have a shape corresponding to an equipped body part, and may have a rectangular shape (in other words, a sheet shape) or the like rather than the cylindrical shape.

[Regarding Configuration of Input Device]

FIG. 2 is a block diagram showing an example of a configuration of the input device 10 related to this embodiment. As exemplified in FIG. 2, the input device 10 related to this embodiment mainly includes the plurality of electrodes 103 and a plurality of amplification units 105 corresponding to N channels, a switch unit 107, an amplification unit 109, an A/D conversion unit 111, and a control unit 113. Also, the input device 10 related to this embodiment may further include a motion identification unit 115 and a storage unit 117.

FIG. 2 shows that one channel includes one electrode 103. However, it is necessary to pay attention to the fact that in FIG. 2, an electrode 103 constituting one channel may be one electrode 103 as described above, or a plurality of electrodes 103.

The plurality of electrodes 103a to 103n corresponding to the N channels sense electromyogram signals that are generated from a muscular fiber group in the body surface B on which the respective electrodes 103 are disposed. In this way, it is possible to acquire planar distribution of electromyogram signals in a body surface around the electrodes 103. Since the electromyogram signals detected by the electrodes 103a to 103n are weak signals, the detected electromyogram signals are output to the amplification units 105a to 105n, which will be described later, and amplified to a predetermined level.

The plurality of amplification units 105a to 105n are installed for the respective electrodes 103a to 103n, and amplify the weak electromyogram signals detected by the respective electrodes 103a to 103n to a degree at which a signal process performed in a subsequent stage can be carried out. When the weak electromyogram signals detected by the respective electrodes 103a to 103n are amplified by the amplification units 105a to 105n installed to correspond to the respective electrodes, it is possible to certainly detect the weak electromyogram signals from the body surface B. These amplification units 105a to 105n can be well-known amplifiers or amplification circuits.

The electromyogram signals that are detected by the respective electrodes 103a to 103n and amplified by the amplification units 105a to 105n corresponding to the respective electrodes are output to the switch unit 107 which will be described later.

The switch unit 107 switches one electromyogram signal output to the amplification unit 109, which will be described later, among the N kinds of electromyogram signals output from the plurality of amplification units 105a to 105n according to a control signal output from the control unit 113 which will be described later. In this way, the N kinds of electromyogram signals (in other words, an electromyogram signal corresponding to any one channel among the electromyogram signals obtained by the electrodes or the electrode group of the N channels) are output to the amplification unit 109 which will be described later. The switch unit 107 can be formed using a well-known multiplexer and the like.

The amplification unit 109 amplifies the electromyogram signal output from the switch unit 107 to a sufficient degree that an A/D conversion process (sampling process) performed in a subsequent stage can be carried out. According to necessity, the amplification unit 109 may perform a filter process using a high-pass filter, a low-pass filter, a band-pass filter, or the like on the amplified electromyogram signal. The electromyogram signal that has been amplified and has undergone the filter process according to necessity is output to the A/D conversion unit 111.

The A/D conversion unit 111 samples the amplified electromyogram signal, which is an analog signal output from the amplification unit 109, and converts the sampled analog signal into a digital signal. The A/D conversion unit 111 outputs the electromyogram signal that has been converted into the digital signal to the motion identification unit 115 which will be described later. Also, the A/D conversion unit 111 may store the electromyogram signal that has been converted into the digital signal in the storage unit 117, which will be described later, and the like as history information.

The control unit 113 controls the switch process of the switch unit 107 for the electromyogram signal output from the electrode and the sampling process of the A/D conversion unit 111 to be synchronized with each other. When detection of an electromyogram signal is performed to correspond to each motion that becomes an identification target, the control unit 113 causes the A/D conversion unit 111 to rapidly perform A/D conversion as many times as the number of the channels. In addition to this, the control unit 113 controls the switch unit 107 so that switch manipulation is performed by the switch unit 107 at the timing of A/D conversion by the A/D conversion unit 111.

For example, when it is assumed that a sampling process is performed on 10 channels at 1 kHz, the control unit 113 causes the switch unit 107 to perform a switch of channels at a rate of 10 kHz and also the A/D conversion unit 111 to perform a sampling process at a rate of 10 kHz, thereby causing such a switch of electrodes and such an A/D conversion process to be repeated until an observed motion ends. Specifically, the control unit 113 repeatedly performs a switch of electrodes 103 constituting one channel and A/D conversion as many times as the number of all the channels (n times) every $t_{smp}=1/n$ (ms) until a motion end time (for example, $t_{end}=1000$ (ms)). In this way, in the input device 10 related to this embodiment, it becomes possible to time-divisionally acquire electromyogram signals corresponding to all the channels. Here, a value of the parameter $t_{end}$ for identifying the motion end time is not limited in particular, and may be appropriately determined by the input device 10 related to this embodiment according to an observed motion.

Also, the control unit 113 supervises a calibration process that is performed in order to select an electrode at an optimum position used to identify a motion which is determined as an identification target of the input device 10 related to this embodiment (referred to as an identification-target motion below) based on an electromyogram signal. The calibration process that is supervised and performed by the control unit 113 will be described in brief below.

In the input device 10 related to this embodiment, at least one channel that detects an electromyogram signal for identifying an identification-target motion such as bending and straightening of each of a user's fingers, motions in and outside a cycle, or the like is selected from among a plurality of channels arranged in a direction that crosses a muscular fiber direction at a right angle.

The number of channels used for identifying the identification-target motion is not limited in particular, and may be appropriately determined in consideration of the degree of precision in identification necessary for the input device 10 related to this embodiment, permissible identification process time, or the like.

The control unit 113 may select the channel that does not overlap channels used in identifying other motions as much as possible from among channels which detect electromyogram signals having signal-to-noise ratios (SNRs) that are equal to or greater than a predetermined threshold value. When the input device 10 related to this embodiment is installed on a body surface such as a forearm or the like, presence of an electrode that does not sufficiently come in contact with the skin may result in a probability that there will be a channel unable to obtain an accurate electromyogram signal. For this reason, by selecting the channel that detects an electromyogram signal having an SNR that is equal to or greater than the predetermined threshold value (in other words, a channel that detects an electromyogram signal that does not overlap much noise), it is possible to improve the degree of precision in detecting electromyogram signals. Also, by selecting channels used for identification between identification-target motions (electrodes that feature in the identification-target motions) not to overlap as much as possible, it is possible to improve the degree of precision in identifying the identification-target motions.

When the calibration process as described above is finished, the control unit 113 generates electrode selection information that presents the selected channel and a position of the channel on the substrate 101. The control unit 113 may store this electrode selection information in the storage unit 117 which will be described later, or the like. A form of the electrode selection information is not limited in particular, and may be stored in the storage unit 117 and the like in a form such as a look-up table or stored in the storage unit 117 as a database. In connection with a maximum of average amplitudes of electromyogram signals, various kinds of other information, or the like that is used as an evaluation value of the electromyogram signal (electromyogram signal evaluation value), the control unit 113 may use the electrode selection information as mentioned above for an electrode calibration process (a simple calibration process which will be described later) involved in deviation of installation positions which will be described later.

When a combination of channels used in identification is selected, the control unit 113 may store a combination of electromyogram signals obtained by the selected channels in the storage unit 117, which will be described later, as a registration template used in a motion identification process in connection with an electrode selection signal.

Preferably, the calibration process is performed at least when a user equips himself or herself with the input device 10 related to this embodiment for the first time. A timing for performing the calibration process is not limited to the aforementioned case. The calibration process may be performed every time a user equips himself or herself with the input device 10 related to this embodiment, at predetermined periods, or at an arbitrary timing according to user manipulation. Also, the control unit 113 may update the electrode selection information stored in the storage unit 117 and the like every time the calibration process is performed.

A detailed example of the calibration process supervised and performed by the control unit 113 will be described again below.

According to the result of the calibration process, the control unit 113 may control operation of the A/D conversion unit 111 so that an electromyogram signal detected by a non-selected electrode is not output from the A/D conversion unit 111 to the motion identification unit 115. In this way, it is possible to reduce load necessary for a motion identification process of the motion identification unit 115, which will be described later, so that the motion identification process can be performed at higher speed, or the degree of precision in motion identification can be further improved.

Also, the control unit 113 supervises a simple calibration process that is a result of simplifying the calibration process performed when the input device 10 related to this embodiment is installed on a user. The simple calibration process supervised and performed by the control unit 113 will be described in brief below.

According to an installation method of the input device 10 related to this embodiment, a relative positional relationship between a certain spot of a body surface and a certain electrode is considered to vary every time the input device 10 is installed. Also, since a user repeats a motion, the input device 10 related to this embodiment deviates, and a relative positional relationship between a body surface (more specifically, a certain muscular fiber group) and an electrode is considered to vary. For this reason, in order to correct a change in a relative positional relationship between a muscular fiber group and an electrode that is involved in installation deviation of the input device 10, a calibration process for selecting a channel used in motion identification is performed in the input device 10 related to this embodiment.

At this time, the control unit 113 may not perform a calibration process as described above but may perform a simple calibration method as described below using electrode selection information or the like which has been generated in a previous calibration process.

In other words, the control unit 113 can identify at least one electrode 103 that has been selected in a previously performed calibration process with reference to electrode selection information, and calibrates the at least one electrode 103 according to a change in a relative positional relationship between the identified at least one electrode 103 and a muscular fiber group.

For example, a change in a positional relationship involved in installation deviation as mentioned above is considered to be about several centimeters, and the number of electrodes 103 that correspond to such an amount of deviation and are arranged in a direction that crosses a muscular fiber group at a right angle is considered to be about 1 or 2. For this reason, the control unit 113 may time-divisionally cause an electrode 103 selected in a previous calibration process and electrodes disposed around the electrode 103 (for example, m electrodes that neighbor each other on upper, lower, left and right sides of the electrode 103) to detect an electromyogram signal while switching between the electrode 103 and the electrodes, and use an electrode that detects an electromyogram signal having a favorable signal-to-noise ratio in motion identification.

Here, the control unit 113 estimates a position of the electrode 103 using the electromyogram signal evaluation value related to the electromyogram signal and the electrode selection information, thereby identifying the amount of a change in a relative positional relationship between the electrode 103 selected in the previous calibration process and the muscular fiber group.

In other words, the control unit 113 actually causes an electromyogram signal to be detected using the electrode 103 recorded in the electrode selection information and electrodes disposed around the electrode, and calculates the electromyogram signal evaluation value. After that, the control unit 113 calculates each correlation between the obtained electromyogram signal evaluation value and an electromyogram signal evaluation value that has been stored as the electrode selection information, thereby identifying distribution of correlation values. By identifying a position of an electrode at which a correlation value is maximized with reference to the identified distribution of correlation values, the control unit 113 can identify the amount of relative deviation between the position of the electrode that has been stored as the electrode selection information and an actual position of the electrode. The control unit 113 becomes able to calibrate an electrode in use according to the identified amount of deviation. In addition, an electromyogram signal evaluation value used in a simple calibration process as described above is not limited in particular, and, for example, a maximum of average amplitudes of electromyogram signals, or the like can be used.

When an electrode calibration process is performed using the electrode selection information stored in the storage unit 117 and the like as described above, it becomes possible to simply perform the electrode calibration process, so that user convenience can be further improved.

A detailed example of the simple calibration process supervised and performed by the control unit 113 will be described again below.

The control unit 113 of the input device 10 related to this embodiment has been described in detail above.

Based on the digital signal that is output from the A/D conversion unit 111 and relates to the electromyogram signal, the motion identification unit 115 identifies what kind of motion a motion corresponding to the electromyogram signal is.

In the input device 10 related to this embodiment, a combination of electromyogram signals is made to correspond to each motion that is determined as an identification target, and stored in advance as a registration template in the storage unit 117, which will be described later, or the like. When the input device 10 related to this embodiment is installed on a user, a calibration process (or a simple calibration process) as described above is performed to correct installation deviation between the input device 10 and the user's body surface (for example, a forearm), and an electrode 103 (more specifically, a channel) used in motion identification is selected.

The motion identification unit 115 compares each registration template as mentioned above with the electromyogram signal obtained by the electrode selected in the calibration among all the electromyogram signals of the electrodes 103 (channels) output from the A/D conversion unit 111, and identifies a registration template most similar to the electromyogram signal output from the A/D conversion unit 111. The motion identification unit 115 identifies that a motion made to correspond to the registration template that is determined to be most similar as a result of such a process is a motion performed by the user.

The motion identification unit 115 may update a registration template corresponding to the identification result using an identified electromyogram signal of the corresponding motion. In this way, in the input device 10 related to this embodiment, the degree of precision in motion identification can be further improved. As a method for updating the registration template, a so-called machine learning technique, a variety of statistical processes, or the like can be employed, or another well-known technique can be applied.

The motion identification unit 115 may output information representing the identification result of the motion performed by the user to a variety of devices installed outside the input device 10. In order to use the motion identification result as a control parameter for performing a variety of functions or services that can be provided to the user by the input device 10, the motion identification unit 115 may output the information to a variety of function control units or service provision units (not shown) of the input device 10. Also, the motion identification unit 115 may display the identification result of the motion performed by the user on a display window installed in the input device 10, a variety of displays (not shown), or the like. Furthermore, the motion identification unit 115 may store time information about the date and time at which the information representing the motion identification result is generated, and the like as history information in the storage unit 117, which will be described below, or the like in connection with the information representing the motion identification result.

The storage unit 117 is implemented by a ROM, a storage device, or the like of the input device 10. In the storage unit 117, the electrode selection information generated in the calibration process described above is stored. Also, in the storage unit 117, a combination of electromyogram signals corresponding to an identification-target motion may be stored as a registration template. Further, in the storage unit 117, a variety of programs run by the input device 10 related to this embodiment, various parameters that it becomes necessary to save when a certain process is performed, interim proceedings and the like of a process, a variety of databases, and the like may be appropriately recorded. The A/D conversion unit 111, the control unit 113, the motion identification unit 115, and the like can freely access the storage unit 117 and write or read data.

An example of a function of the input device 10 related to this embodiment has been presented above. Each of the components may be a general-purpose member or circuit, or may be hardware that specializes in functions of the component. Also, all functions of each component may be performed by a CPU or the like. Thus, it is possible to appropriately change a configuration in use according to a technology level any time this embodiment is implemented.

<Regarding Calibration Method and Input Method>

Figure 3:
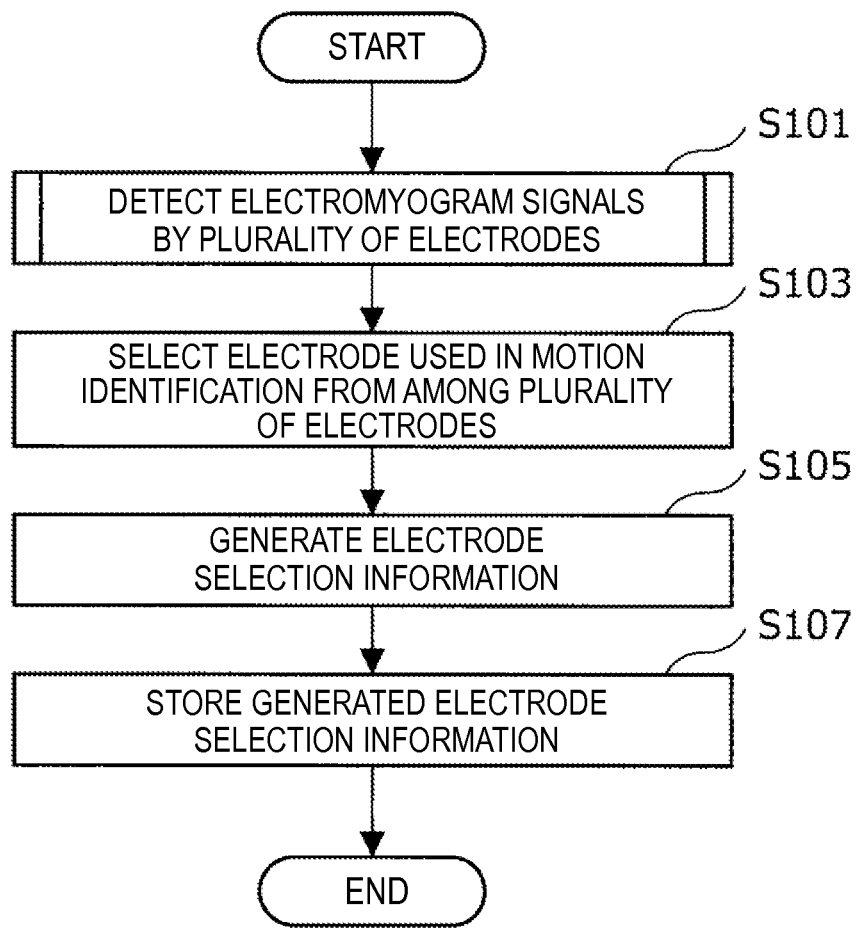
FIG. 3 is a flowchart showing an example of the flow of a calibration method related to the same embodiment.
Figure 4:
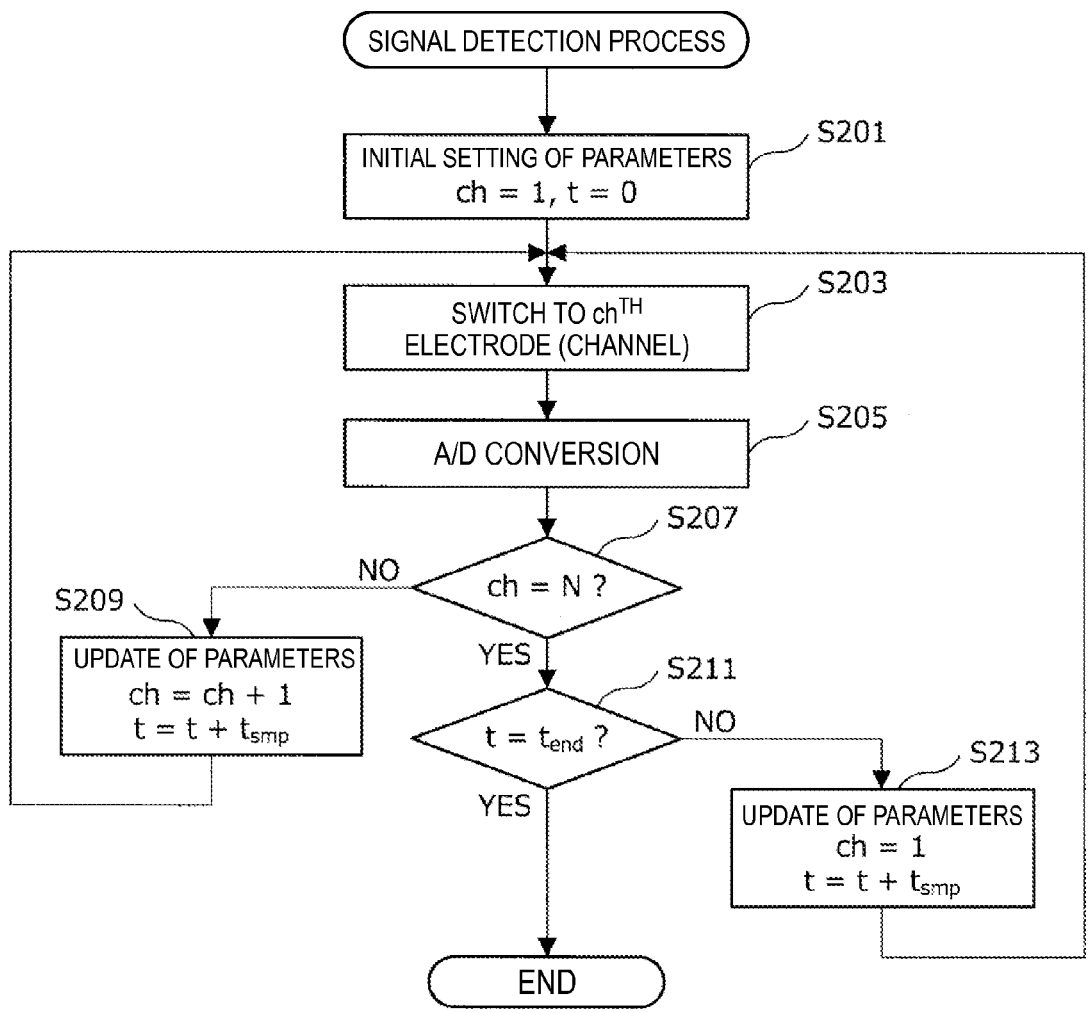
FIG. 4 is a flowchart showing an example of the flow of an electromyogram signal detection method related to the same embodiment.
Figure 5:
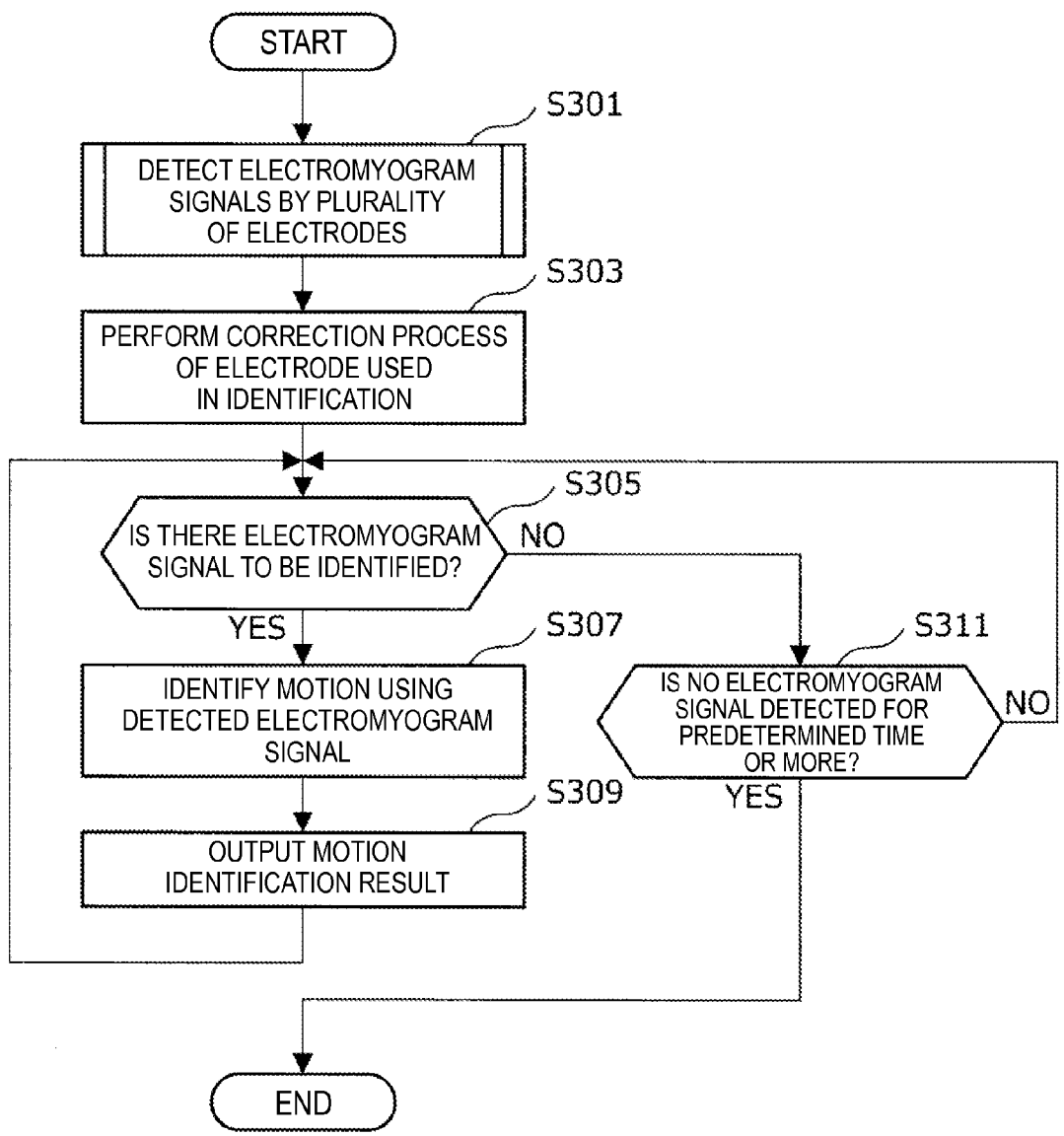
FIG. 5 is a flowchart showing an example of the flow of an input method related to the same embodiment.

With reference to FIG. 3 to FIG. 5, descriptions will be made on an example of the flow of a calibration method performed by the input device 10 related to this embodiment and an input method including the calibration method. FIG. 3 is a flowchart showing an example of the flow of a calibration method related to this embodiment. FIG. 4 is a flowchart showing an example of the flow of an electromyogram signal detection process related to this embodiment. FIG. 5 is a flowchart showing an example of the flow of an input method related to this embodiment.

[Regarding Flow of Calibration Method]

First, an example of the flow of a calibration method will be described in brief with reference to FIG. 3.

In the input device 10 related to this embodiment, the plurality of electrodes 103, the amplification units 105, the switch unit 107, the amplification unit 109, the A/D conversion unit 111, and the control unit 113 interoperate with each other, and thereby electromyogram signals are detected by a plurality of electrodes (step S101).

After that, the control unit 113 selects an electrode used for motion identification from among the plurality of electrodes using the detected electromyogram signals (step S103).

When selection of an electrode is finished, the control unit 113 generates electrode selection information about information about the electrode used for identifying an identification-target motion (step S105). After that, the control unit 113 stores the generated electrode selection information in the storage unit 117 and the like (step S107).

[Regarding Flow of Electromyogram Signal Detection Process]

Here, the plurality of electrodes 103 and amplification units 105, the switch unit 107, the amplification unit 109, the A/D conversion unit 111, and the control unit 113 interoperate with each other, and an electromyogram signal detection process is performed in the flow as shown in FIG. 4.

In other words, the control unit 113 first performs initial setting of parameters used for a switch of the plurality of electrodes 103 (step S201). A parameter ch is used for selecting an electrode (channel) that detects an electromyogram signal output to the amplification unit 109 by the switch unit 107, and a parameter t represents an elapsed process time.

Subsequently, the control unit 113 controls the switch unit 107 to switch the output of a $ch^{th}$ electrode (channel) (step S203). In this way, the switch unit 107 outputs an electromyogram signal that is output from an electrode 103 corresponding to a channel ch to the amplification unit 109. The amplification unit 109 amplifies the electromyogram signal that is output from the electrode 103 corresponding to the channel ch, and outputs the amplified electromyogram signal to the A/D conversion unit 111. After that, the A/D conversion unit 111 A/D-converts the electromyogram signal that is output from the electrode 103 corresponding to the channel ch (step S205).

Next, the control unit 113 determines whether or not a value of the parameter ch is equal to a value N representing the number of entire channels (step S207). When the value of the parameter ch is not equal to the number N of entire channels, the control unit 113 updates values of the parameter ch and the parameter t (step S209). In other words, the control unit 113 increases the value of the parameter ch by 1, and also adds a time $t_{smp}$ necessary for a sampling process by the A/D conversion unit 111 to a value of the parameter t. After that, the process returns to step S203, and the control unit 113 continues the electromyogram signal detection process.

On the other hand, when the value of the parameter ch is equal to the number N of entire channels in step S207, the control unit 113 determines whether or not the value of the parameter t representing the time is equal to a motion end time $t_{end}$ (step S211). When the value of the parameter t is not equal to the motion end time $t_{end}$, the control unit 113 updates values of the parameter ch and the parameter t (step S213). In other words, the control unit 113 sets the value of the parameter ch to 1, and also adds the time $t_{smp}$ necessary for a sampling process by the A/D conversion unit 111 to a value of the parameter t. After that, the process returns to step S203, and the control unit 113 continues the electromyogram signal detection process.

On the other hand, when the value of the parameter t is equal to the motion end time $t_{end}$ in step S211, the control unit 113 finishes the electromyogram signal detection process.

By performing the process in the flow as described above, the input device 10 related to this embodiment can select an electrode used for detecting an electromyogram signal which is used in identifying an identification-target motion from among a plurality of electrodes.

[Regarding Flow of Input Method]

Next, an example of the flow of an input method will be described in brief with reference to FIG. 5.

When the input device 10 related to this embodiment is installed on a user, first, the plurality of electrodes 103 and amplification units 105, the switch unit 107, the amplification unit 109, the A/D conversion unit 111, and the control unit 113 interoperate with each other, and thereby an electromyogram signal is detected (step S301). This electromyogram signal detection process is performed as in the flow shown in FIG. 4. After that, the control unit 113 performs a calibration process of an electrode used in identification using the detected electromyogram signal (step S303).

Subsequently, the motion identification unit 115 determines whether or not there is an electromyogram signal to be identified (step S305). When there is an electromyogram signal to be identified, the motion identification unit 115 identifies a motion corresponding to the detected electromyogram signal using the electromyogram signal (step S307). After that, the motion identification unit 115 outputs information related to the identification result of the motion to a device or a process unit that uses the identification result (step S309).

On the other hand, when there is no electromyogram signal to be identified in step S305, the motion identification unit 115 determines whether or not no electromyogram signal is detected for a predetermined time or more (step S311). When a time for which no electromyogram signal is detected is less than a predetermined threshold value, the process returns to step S305, and the motion identification unit 115 waits for an electromyogram signal. When the time for which no electromyogram signal is detected is the predetermined threshold value or more, the motion identification unit 115 finishes the process.

An example of the flow of a calibration method performed by the input device 10 related to this embodiment and an input method including an electrode calibration method has been described above with reference to FIG. 3 to FIG. 5.

<Detailed Examples of Calibration Method and Simple Calibration Method>

Next, a calibration method and a simple calibration method performed by the input device 10 related to this embodiment will be described with reference to detailed examples. The detailed examples of calibration methods presented below are merely examples of a calibration method and a simple calibration method related to this embodiment, and the calibration method performed by the input device 10 related to this embodiment is not limited to the example below.

[Detailed Example of Calibration Method]

Figure 6:
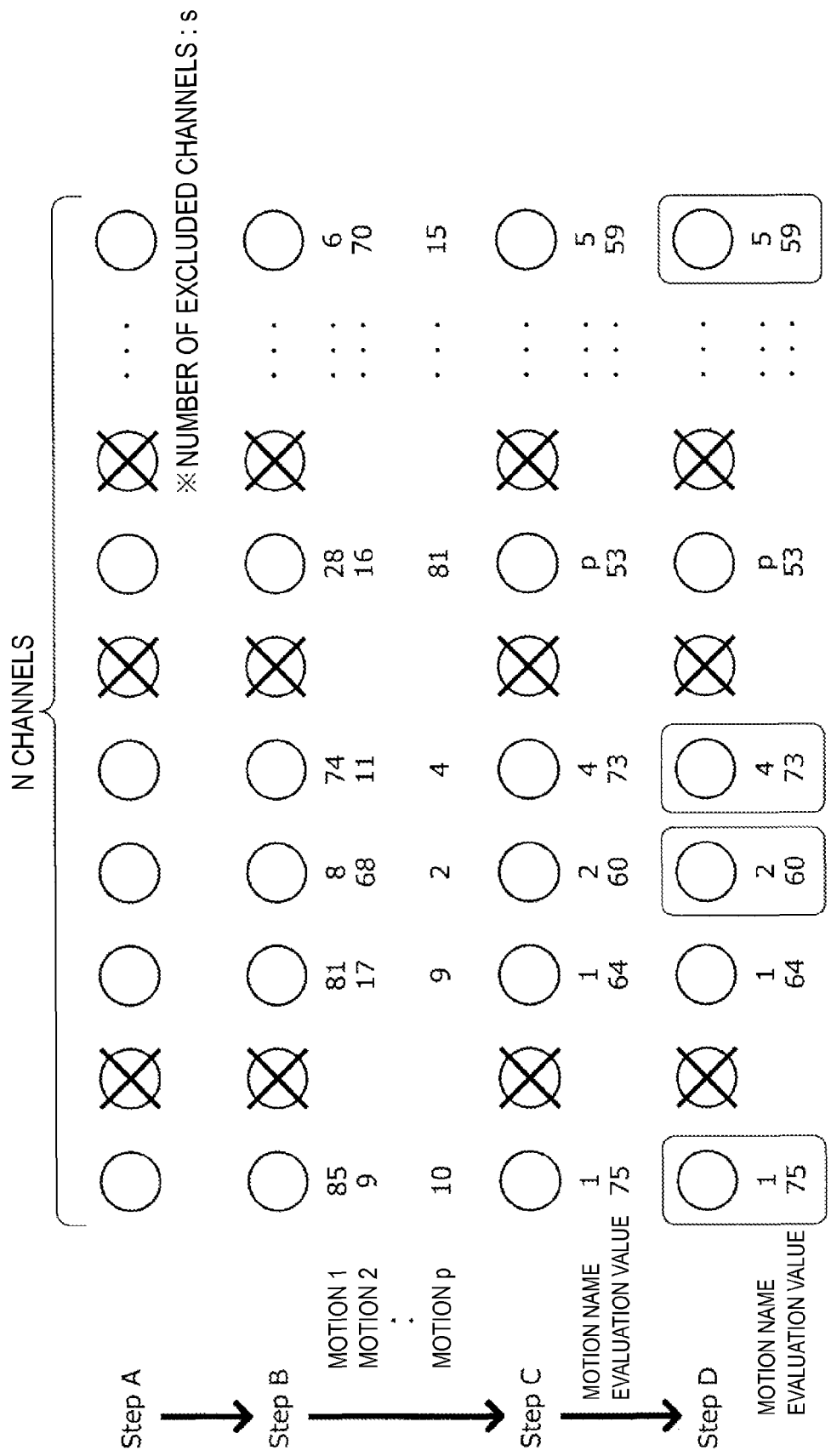
FIG. 6 is an explanatory diagram illustrating a detailed example of the calibration method related to the same embodiment.

First, the flow of a detailed example of the calibration method related to this embodiment will be described in brief with reference to FIG. 6. FIG. 6 is an explanatory diagram illustrating a detailed example of the calibration method related to this embodiment.

A case of selecting r channels (electrodes) from among N channels (electrodes) will be described below as an example of a calibration process for identifying p types of identification-target motions.

First, the control unit 113 excludes a channel that detects an electromyogram signal overlapped by a large artifact of a predetermined threshold value or more with reference to electromyogram signals detected by N channels with respect to each of p types of motions (Step A). An example of the artifact can be a reduction in electromyogram signal intensity caused by detachment of an electrode 103 from the body surface B, a motion artifact caused by a wobble and the like of a cable and the like installed in the input device 10, overlap of alternating current, overlap of heartbeats, or the like.

In FIG. 6, when a large artifact of the predetermined threshold value or more overlaps electromyogram signals detected by s channels, the control unit 113 excludes the s channels, and selects a channel used in an identification process from among (N-s) other channels.

Next, the control unit 113 calculates average amplitudes, such as Average Rectified Values (ARVs), Root Mean Square (RMSs), or the like, of electromyogram signals obtained by the (N-s) channels with respect to each of the p types of motions, and identifies a maximum of the average amplitudes (Step B). Here, an average rectified value is obtained by calculating an absolute value of an amplitude (rectification) and then integrating the calculated absolute value of the amplitude over a predetermined time or using a low-pass filter. Also, a root mean square is obtained by extracting the square root of an average of squares of electromyogram signals within a predetermined time.

In the example shown in FIG. 6, a maximum of average amplitudes corresponding to the respective (N-s) channels is calculated with respect to each motion by the control unit 113.

Subsequently, with respect to each of the (N-s) channels, the control unit 113 calculates a motion name of a motion giving a largest value among maximums of average amplitudes of the respective motions calculated in Step B, and subtracts a maximum giving a second largest value from a maximum giving the largest value (Step C). For example, the leftmost channel in FIG. 6 will be discussed. With respect to this channel, a maximum of average amplitudes that gives the largest value is a maximum of 85 corresponding to motion 1, and a maximum that gives the second largest value is a maximum of 10 corresponding to motion p. In this case, the control unit 113 determines the motion name "motion 1" and a value of 85−10=75 as an evaluation value of this channel. In the same manner, the control unit 113 calculates motion names and evaluation values with respect to the (N-s) channels.

Next, the control unit 113 selects r values calculated in Step C in order of decreasing value (Step D). At this time, the control unit 113 excludes a channel corresponding to a motion name that has already been determined from selection.

In addition, when r>p is satisfied, the control unit 113 selects p channels in Step D, and then perform Step D again on the other channels, thereby selecting a total of r channels.

When such a calibration process is performed under the supervision of the control unit 113, an electrode that has a signal-to-noise ratio of a predetermined threshold value or more is selected so that crosstalk in each motion becomes as small as possible.

[Detailed Example of Simple Calibration Method]

Next, the flow of a detailed example of the simple calibration method related to this embodiment will be described in brief.

Descriptions will be made below of a case in which deviation of an electrode disposition (an input device for an arm or a foot or the like, and in the case of a cylindrical-shape input device, an unfolded electrode disposition) from an installation position upon a previously performed calibration process is as large as one upper, lower, left or right channel or less. In descriptions below, a vertical direction in an electrode disposition denotes a direction along a muscular fiber group, and a horizontal direction in the electrode disposition denotes a direction that crosses the muscular fiber group at a right angle. Depending on an electrode disposition, there may be no electrode in an upward direction or a downward direction of an observed electrode.

Also, it is assumed that information about a maximum of average amplitudes of electromyogram signals corresponding to the N channels with respect to each of the p types of identification-target motions and positions of the r selection channels is made to correspond to electrode selection information stored in the storage unit 117 and the like.

First, the control unit 113 selects one arbitrary motion from among the p types of identification-target motions, and causes electromyogram signals of all the channels to be detected. After that, like in the calibration process described above, the control unit 113 excludes a channel that detects an electromyogram signal overlapped by a large artifact.

Next, the control unit 113 calculates a maximum of average amplitudes, for example, average rectified values, root mean squares, or the like, of detected electromyogram signals. After that, the control unit 113 acquires a maximum of average amplitudes with respect to the one selected motion that is recorded in the electrode selection information with reference to the stored electrode selection information, and finds a correlation between the acquired maximum and the maximum of average amplitudes calculated this time.

In the same manner, the control unit 113 also finds a correlation between a maximum of average amplitudes of a case in which the maximum of average amplitudes recorded in the electrode selection information with respect to the one selected motion is shifted as much as one upper, lower, left or right channel and the maximum of average amplitudes calculated this time. In this way, the control unit 113 can find a distribution situation of correlation values.

After that, the control unit 113 identifies a position of the largest correlation value based on the distribution situation of correlation values, and finds the amount of installation deviation (amount of deviation). In this way, the control unit 113 can correct the installation deviation, and select r electrodes corresponding to installation of this time.

Detailed examples of the calibration method and the simple calibration method performed by the input device 10 related to this embodiment have been described in brief above.

Modified Example

Figure 7:
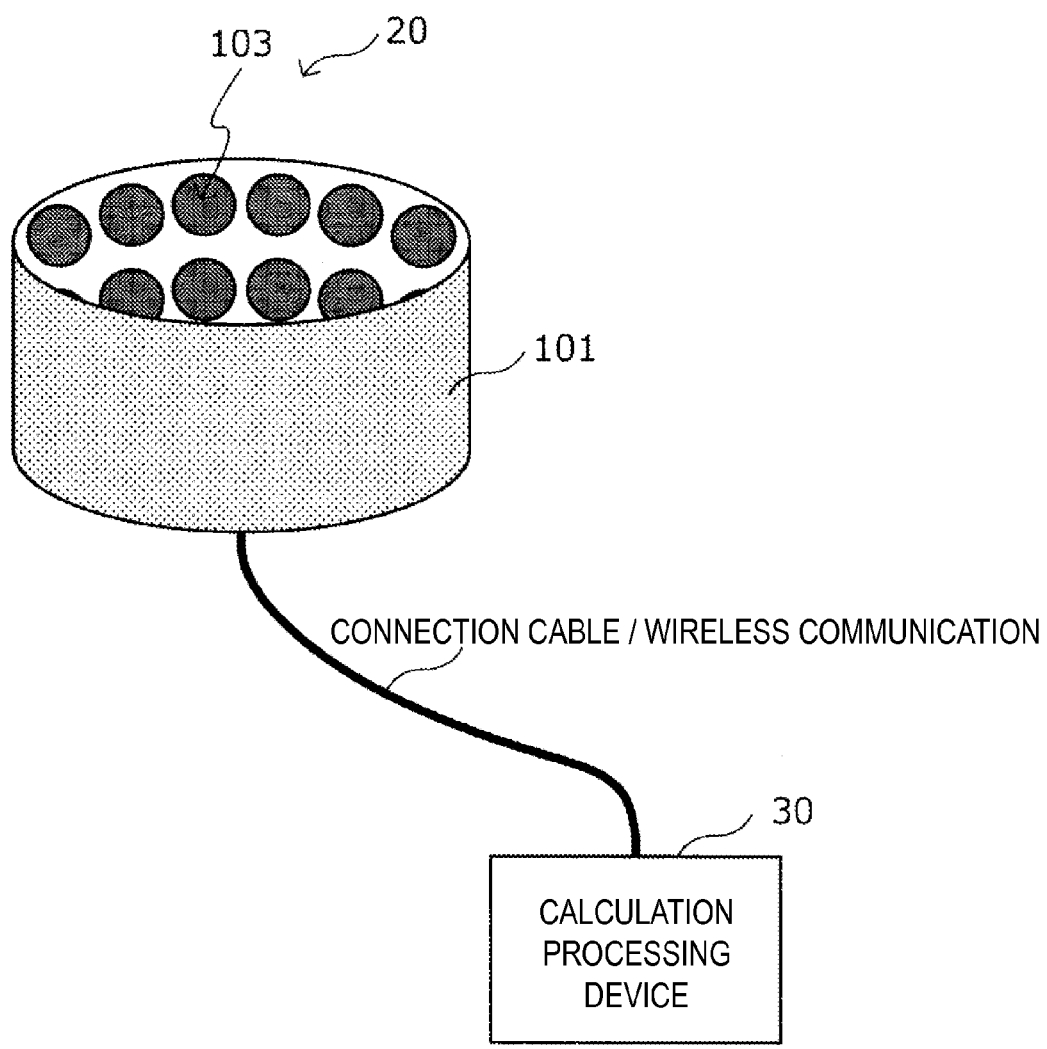
FIG. 7 is an explanatory diagram illustrating a modified example of the input device related to the same embodiment.
Figure 8:
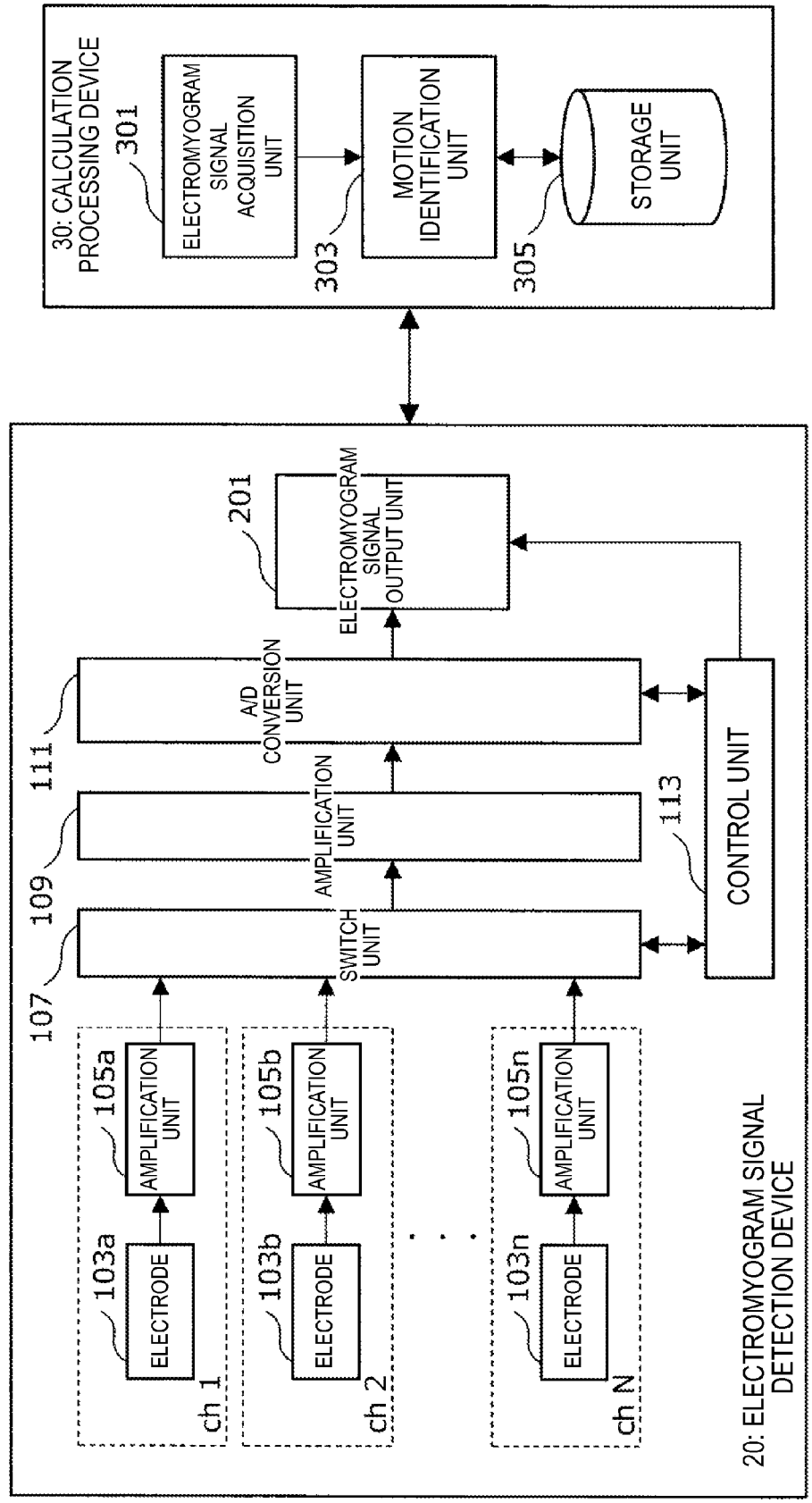
FIG. 8 is an explanatory diagram illustrating the modified example of the input device related to the same embodiment.

Next, with reference to FIG. 7 and FIG. 8, a modified example of the input device 10 related to this embodiment will be described in brief. FIG. 7 and FIG. 8 are explanatory diagrams illustrating a modified example of the input device 10 related to this embodiment.

Functions of respective process units shown in FIG. 2 other than the electrodes 103 and the amplification units 105 may be accommodated in any piece of hardware among respective pieces of hardware that can exchange information with each other via a network. Also, a process performed by a certain process unit may be implemented by one piece of hardware or through a distributed process by a plurality of pieces of hardware.

For example, as shown in FIG. 7, functions of the input device 10 shown in FIG. 2 may be distributed to and implemented by an electromyogram signal detection device 20 that detects an electromyogram signal and a calculation processing device 30 that performs a calculation process. The electromyogram signal detection device 20 and the calculation processing device 30 may be connected by wire through a connection cable or the like as shown in FIG. 7, or connected through wireless communication.

FIG. 8 shows an example of a configuration of the electromyogram signal detection device 20 and the calculation processing device 30 when functions of the motion identification unit 115 shown in FIG. 2 are accommodated in the calculation processing device 30 that is connected with the electromyogram signal detection device 20 by wire or wirelessly.

As shown in FIG. 7 and FIG. 8, the electromyogram signal detection device 20 mainly includes a plurality of electrodes 103 arranged on a substrate 101, a plurality of amplification units 105, a switch unit 107, an amplification unit 109, an A/D conversion unit 111, a control unit 113, and an electromyogram signal output unit 201.

Here, the plurality of electrodes 103 arranged on the substrate 101, the plurality of amplification units 105, the switch unit 107, the amplification unit 109, the A/D conversion unit 111, and the control unit 113 have the same configurations as the respective process units in the input device 10 shown in FIG. 2 and bring about the same effects. Accordingly, detailed descriptions will be omitted below.

The electromyogram signal output unit 201 outputs digital data of an electromyogram signal output from the A/D conversion unit 111 to the calculation processing device 30. Digital data communication from the electromyogram signal detection device 20 to the calculation processing device 30 may be performed through a connection cable as shown in FIG. 7, or through well-known wireless communication.

As shown in FIG. 8, the calculation processing device 30 mainly includes an electromyogram signal acquisition unit 301, a motion identification unit 303, and a storage unit 305.

The electromyogram signal acquisition unit 301 acquires digital data of the electromyogram signal that is output from the electromyogram signal detection device 20, and outputs the acquired digital data to the motion identification unit 303.

The motion identification unit 303 and the storage unit 305 have the same configurations as the motion identification unit 115 and the storage unit 117 in the input device 10 shown in FIG. 2 and bring about the same effects. Accordingly, detailed descriptions will be omitted below.

When a part that detects an electromyogram signal and a part that performs a motion identification process are implemented in a distributed manner as shown in FIG. 7 and FIG. 8, the weight of the electromyogram signal detection device 20 that is installed on a body surface can be reduced, and user convenience can be improved.

With reference to FIG. 7 and FIG. 8, the modified example of the input device 10 related to this embodiment has been described in brief above.

(Summary)

As described above, since an input device related to an embodiment of the present disclosure causes a plurality of electrodes installed on a body surface to operate while switching between the plurality of electrodes and performs a motion identification process using some of electromyogram signals obtained from the plurality of electrodes, it becomes possible to reduce the load of signal processing. In this way, a response time necessary for motion identification can be further reduced.

Since a calibration process is performed upon installation of an input device related to an embodiment of the present disclosure, it becomes unnecessary to accurately determine positions of electrodes, and the installation is facilitated. In the second and the following calibrations, a calibration process is simply performed using saved calibration information, and an electrode position is estimated, so that the process can be reduced. Also, even if motions in and outside a cycle are performed during motion identification, such an electrode calibration process enables the degree of precision in motion identification to be maintained.

An input device related to an embodiment of the present disclosure can be applied to, for example, a game controller, a remote controller of a stationary device, such as a TV, a personal computer, and the like, controllers of a variety of portable devices, and the like. Also, an input device related to an embodiment of the present disclosure can be applied to medical or nursing technology.

Although the preferred embodiments of the present invention have been described in detail with reference to the appended drawings, the present invention is not limited thereto. It is obvious to those skilled in the art that various modifications or variations are possible insofar as they are within the technical scope of the appended claims or the equivalents thereof. It should be understood that such modifications or variations are also within the technical scope of the present invention.

Additionally, the present application may also be configured as below.

(1) An input device including:
a plurality of electrodes that are arranged on a surface of a body in a direction crossing a muscular fiber group of the body at a right angle, and detect electromyogram signals generated from the muscular fiber group according to a motion performed by the body;
a switch unit that switches an electrode acquiring an electromyogram signal between the plurality of electrodes; and
a control unit that selects an electrode detecting an electromyogram signal for identifying the motion from among the plurality of electrodes.

(2) The input device according to (1),
wherein the control unit selects the at least one electrode detecting the electromyogram signal for identifying the motion based on the respective electromyogram signals acquired by the plurality of electrodes.

(3) The input device according to (2),
wherein the control unit selects the electrode having detected the electromyogram signal having a signal-to-noise ratio of a predetermined threshold value or more from among the plurality of electrodes so that an overlap with electrodes used in identifying other motions becomes small.

(4) The input device according to (1),
wherein the control unit calibrates an electrode used as the at least one electrode according to a change in a relative positional relationship between the at least one electrode detecting the electromyogram signal for identifying the motion and the muscular fiber group.

(5) The input device according to (2), further including:
a storage unit that stores electrode selection information representing a combination of the electrodes for detecting the electromyogram signal used for identifying the motion.

(6) The input device according to (5),
wherein the control unit identifies an amount of change in a relative positional relationship between the at least one electrode detecting the electromyogram signal for identifying the motion and the muscular fiber group by estimating a position of the electrode using an electromyogram signal evaluation value of the electromyogram signal and the electrode selection information, and calibrates an electrode used as the at least one electrode.

(7) The input device according to (1), further including:
a motion identification unit that identifies the motion performed by the body using the electromyogram signal detected by the selected electrode.

(8) The input device according to (1),
wherein the surface of the body on which the plurality of electrodes are arranged is a forearm, and
wherein the plurality of electrodes are arranged in a direction of the muscular fibers and a circumferential direction of the forearm.

(9) A calibration method including:
time-divisionally detecting electromyogram signals while switching between a plurality of electrodes that are arranged on a surface of a body in a direction crossing a muscular fiber group of the body at a right angle and detect the electromyogram signals generated from the muscular fiber group according to a motion performed by the body; and
selecting at least one electrode detecting an electromyogram signal for identifying the motion based on the respective electromyogram signals acquired by the plurality of electrodes.

(10) The calibration method according to (9),
wherein electrode selection information representing a combination of the electrodes for detecting the electromyogram signals used for identifying the motion are stored in advance, and
wherein selecting the at least one electrode includes identifying an amount of change in a relative positional relationship between the at least one electrode detecting the electromyogram signal for identifying the motion and the muscular fiber group by estimating a position of the electrode using an electromyogram signal evaluation value of the electromyogram signal and the electrode selection information, and selecting an electrode used as the at least one electrode.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. An input device comprising:
a plurality of electrodes that are arranged on a surface of a body in a direction crossing a muscular fiber group of the body at a right angle, and are configured to detect electromyogram signals generated from the muscular fiber group according to a motion performed by the body;
a switch unit configured to switch an electrode acquiring an electromyogram signal between the plurality of electrodes based on a first parameter and a second parameter; and
a control unit configured to perform setting of the first parameter and the second parameter, wherein the first parameter is used to select an electrode detecting an electromyogram signal for identifying the motion from among the plurality of electrodes and the second parameter represents an elapsed process time,
wherein the control unit is configured to select the at least one electrode detecting the electromyogram signal for identifying the motion based on respective electromyogram signals acquired by the plurality of electrodes, and
wherein the control unit selects the electrode having detected the electromyogram signal having signal-to-noise ratio of a predetermined threshold value or more from among the plurality of electrodes so that an overlap with electrodes used in identifying other motions becomes small.

2. The input device according to claim 1,
wherein the control unit calibrates an electrode used as the at least one electrode according to a change in a relative positional relationship between the at least one electrode detecting the electromyogram signal for identifying the motion and the muscular fiber group.

3. The input device according to claim 1, further comprising:
a storage unit that stores electrode selection information representing a combination of the electrodes for detecting the electromyogram signal used for identifying the motion.

4. The input device according to claim 3,
wherein the control unit identifies an amount of change in a relative positional relationship between the at least one electrode detecting the electromyogram signal for identifying the motion and the muscular fiber group by estimating a position of the electrode using an electromyogram signal evaluation value of the electromyogram signal and the electrode selection information, and calibrates an electrode used as the at least one electrode.

5. The input device according to claim 1, further comprising:

a motion identification unit that identifies the motion performed by the body using the electromyogram signal detected by the selected electrode.

6. The input device according to claim 1,
wherein the surface of the body on which the plurality of electrodes are arranged is a forearm, and
wherein the plurality of electrodes are arranged in a direction of the muscular fibers and a circumferential direction of the forearm.

7. The input device according to claim 1,
wherein the elapsed process time corresponds to a time taken by an analog to digital (A/D) conversion unit for performing a sampling process on the electromyogram signal.

8. A calibration method comprising:
time-divisionally detecting electromyogram signals while switching between a plurality of electrodes that are arranged on a surface of a body in a direction crossing a muscular fiber group of the body at a right angle and detect the electromyogram signals generated from the muscular fiber group according to a motion performed by the body based on a first parameter and a second parameter;
performing setting of the first parameter and the second parameter, wherein the first parameter is used to select at least one electrode detecting an electromyogram signal for identifying the motion based on the respective electromyogram signals acquired by the plurality of electrodes and the second parameter represents an elapsed process time; and
selecting the electrode having detected the electromyogram signal having a signal-to-noise ratio of a predetermined threshold value or more from among the plurality of electrodes so that an overlap with electrodes used in identifying other motions becomes small.

9. The calibration method according to claim 8,
wherein electrode selection information representing a combination of the electrodes for detecting the electromyogram signals used for identifying the motion are stored in advance, and
wherein selecting the at least one electrode includes identifying an amount of change in a relative positional relationship between the at least one electrode detecting the electromyogram signal for identifying the motion and the muscular fiber group by estimating a position of the electrode using an electromyogram signal evaluation value of the electromyogram signal and the electrode selection information, and selecting an electrode used as the at least one electrode.

* * * * *